United States Patent
Gross et al.

(10) Patent No.: US 8,435,033 B2
(45) Date of Patent: May 7, 2013

(54) DENTAL NAVIGATION TECHNIQUES

(75) Inventors: Yossi Gross, Moshav Mazor (IL); Hadar Better, Tel Aviv (IL)

(73) Assignee: Rainbow Medical Ltd., Herzeliya (IL)

( * ) Notice: Subject to any disclaimer, the term of this patent is extended or adjusted under 35 U.S.C. 154(b) by 107 days.

(21) Appl. No.: 12/839,056

(22) Filed: Jul. 19, 2010

(65) Prior Publication Data

US 2012/0015329 A1    Jan. 19, 2012

(51) Int. Cl.
    *A61C 3/00* (2006.01)
(52) U.S. Cl.
    USPC .............................................. 433/75; 433/214
(58) Field of Classification Search ............ 433/72, 433/75, 214
    See application file for complete search history.

(56) References Cited

U.S. PATENT DOCUMENTS

| | | | |
|---|---|---|---|
| 5,230,338 A | 7/1993 | Allen et al. | |
| 5,309,913 A | 5/1994 | Kormos et al. | |
| 5,343,391 A | 8/1994 | Mushabac | |
| 5,347,454 A * | 9/1994 | Mushabac | 433/214 |
| 5,603,318 A | 2/1997 | Heilbrun et al. | |
| 5,740,802 A | 4/1998 | Nafis et al. | |
| 5,769,789 A | 6/1998 | Wang et al. | |
| 5,792,147 A | 8/1998 | Evans et al. | |
| 5,836,954 A | 11/1998 | Heilbrun et al. | |
| 5,954,647 A | 9/1999 | Bova et al. | |
| 5,954,650 A | 9/1999 | Saito et al. | |
| 5,967,777 A | 10/1999 | Klein et al. | |
| 5,989,025 A | 11/1999 | Conley | |
| 6,006,126 A | 12/1999 | Cosman | |
| 6,285,903 B1 * | 9/2001 | Rosenthal et al. | 600/433 |
| 6,319,006 B1 | 11/2001 | Scherer et al. | |
| 6,333,971 B2 | 12/2001 | McCrory et al. | |
| 6,381,485 B1 | 4/2002 | Hunter et al. | |
| 6,450,978 B1 | 9/2002 | Brosseau et al. | |
| 6,491,702 B2 * | 12/2002 | Heilbrun et al. | 606/130 |
| 6,507,751 B2 | 1/2003 | Blume et al. | |
| 6,640,128 B2 | 10/2003 | Vilsmeier et al. | |
| 6,919,867 B2 | 7/2005 | Sauer | |
| 6,978,167 B2 | 12/2005 | Dekel et al. | |
| 7,011,681 B2 | 3/2006 | Vesely | |
| 7,376,903 B2 | 5/2008 | Morita et al. | |
| 7,574,025 B2 | 8/2009 | Feldman | |
| 7,643,867 B2 | 1/2010 | Solar et al. | |
| 7,844,320 B2 * | 11/2010 | Shahidi | 600/424 |
| 7,876,942 B2 | 1/2011 | Gilboa | |
| 7,894,878 B2 | 2/2011 | Noujeim | |

(Continued)

FOREIGN PATENT DOCUMENTS

| WO | WO 91/07726 | 5/1991 |
|---|---|---|
| WO | WO 2006/076789 | 7/2006 |
| WO | WO 2010/031060 | 3/2010 |

*Primary Examiner* — Ralph Lewis
(74) *Attorney, Agent, or Firm* — Sughrue Mion, PLLC

(57) ABSTRACT

Apparatus and methods are described, including at least one tool configured to be placed inside a subject's mouth. A first optically-visible marker is coupled to the tool. A second optically-visible marker is coupled to a structure inside the subject's mouth. A plurality of optical cameras are coupled to the tool, and are placed inside the subject's mouth by the tool being placed inside the subject's mouth. The cameras acquire respective images of the inside of the subject's mouth, in which the second optically-visible marker is identifiable. A plurality of optical cameras that are disposed outside the subject's mouth acquire respective images of the tool, while the tool is inside the subject's mouth, in which images the first optically-visible marker is identifiable. Other embodiments are also described.

8 Claims, 3 Drawing Sheets

U.S. PATENT DOCUMENTS

| | | |
|---|---|---|
| 8,111,239 B2 | 2/2012 | Pryor |
| 8,246,352 B2 * | 8/2012 | Takebayashi .................. 433/75 |
| 2004/0002642 A1 | 1/2004 | Dekel et al. |
| 2004/0138556 A1 | 7/2004 | Cosman |
| 2004/0210125 A1 | 10/2004 | Chen et al. |
| 2005/0182319 A1 | 8/2005 | Glossop |
| 2006/0240378 A1 | 10/2006 | Weinstein et al. |
| 2006/0257817 A1 | 11/2006 | Shelton |
| 2007/0031774 A1 | 2/2007 | Cinader, Jr. et al. |
| 2007/0173861 A1 | 7/2007 | Strommer et al. |
| 2007/0208252 A1 | 9/2007 | Makower |
| 2007/0236514 A1 | 10/2007 | Agusanto et al. |
| 2007/0238981 A1 | 10/2007 | Zhu et al. |
| 2008/0055308 A1 | 3/2008 | Dekel et al. |
| 2008/0057467 A1 | 3/2008 | Gittelson |
| 2008/0074422 A1 | 3/2008 | Dekel et al. |
| 2008/0227056 A1 | 9/2008 | Bulard |
| 2008/0278490 A1 | 11/2008 | Dekel |
| 2009/0042167 A1 | 2/2009 | Van Der Zel et al. |
| 2009/0092948 A1 | 4/2009 | Gantes |
| 2009/0097722 A1 | 4/2009 | Dekel et al. |
| 2010/0121436 A1 | 5/2010 | Tuval et al. |
| 2010/0198346 A1 | 8/2010 | Keogh et al. |
| 2011/0008751 A1 | 1/2011 | Pettersson |
| 2011/0054303 A1 | 3/2011 | Barrick |
| 2011/0060558 A1 | 3/2011 | Pettersson et al. |
| 2011/0130649 A1 | 6/2011 | Strommer |

* cited by examiner

DENTAL NAVIGATION TECHNIQUES

FIELD OF EMBODIMENTS OF THE INVENTION

Some applications of the present invention generally relate to apparatus and methods for dental treatment. Specifically, some applications of the present invention relate to navigation techniques for dental procedures.

BACKGROUND

For some dental procedures, a combination of imaging modalities is used to image the procedure. For example, the subject's bones and teeth are typically imaged using an x-ray-based imaging modality, such as CT. Soft tissue and the other structures in the patient's mouth are imaged using MRI and/or optical imaging techniques, e.g., using digital cameras.

In order to facilitate the co-use of two or more imaging modalities for navigation during a dental procedure, and/or for planning a dental procedure, images acquired by the two modalities are typically registered to each other. Registration is a term that is used to describe one-to-one mapping between the coordinates in one space and those of another, such that points in the two spaces that correspond to the same anatomic point are mapped to each other (c.f., U.S. Pat. No. 5,769,789 to Wang).

In some procedures, in order to facilitate the co-registration of images acquired by two or more imaging modalities, fiducials are identified in images that have been acquired using respective modalities. The term "fiducial" is generally understood in engineering or surveying, to describe a point or marking, or a line, which is sufficiently precisely defined to serve as a standard or basis reference for other measurements (c.f., U.S. Pat. No. 5,603,318 to Heilbrun).

U.S. Pat. No. 6,319,006 to Scherer describes a method for producing a drill assistance device for a tooth implant that includes the process steps of, initially the taking of an x-ray picture of the jaw and the compilation of a corresponding measured data record; then a three-dimensional, optical measurement of the visible surfaces of the jaw and of the teeth and the compilation of a corresponding measured data record. The measured data records from the x-ray picture and the measured data records from the three-dimensional, optical image are correlated with each other. Based on the information that is now available the type and position of the implant relative to the adjacent teeth is planned and a drill template is produced which is attached to the neighboring teeth. This is described as making the exact drilling of the implant pilot hole possible.

US 2008/0057467 to Gittelson describes a prefabricated dental implant surgical guide. The implant surgical guide comprises a tooth-shaped contour which simulates a natural tooth shape and the final prosthesis. An impression of an edentulous area and existing teeth of a patient is taken. A stone model of the impression is then made. A tooth-shaped contour(s) is selected from a tooth-shape and size selector kit comprising tooth-shaped contours, the tooth-shaped contours having central bores and corresponding to the edentulous area are secured to the stone model. A matrix of the stone model is formed with the tooth-shaped contours in place. The matrix is then removed from the stone model while retaining the selected tooth-shaped contour(s). Surgical drill holes are created in the matrix aligned with the central bores of the selected tooth-shaped contours to create the implant surgical guide. The matrix, now functioning as a surgical guide is then placed into the mouth of the patient. An osteotomy site is initiated by placing a surgical drill bur through the surgical drill holes of the matrix and through the central bores of the selected tooth-shaped contours, while the selected tooth-shaped contours are stabilized in their proper position by the matrix. The tooth-shaped contours can also be made of a radio opaque material, which when contained in the matrix and worn by the implant patient allow it to function as a dental scan appliance.

The following references may be of interest:
U.S. Pat. No. 5,230,338 to Allen
U.S. Pat. No. 5,309,913 to Kormos
U.S. Pat. No. 5,343,391 to Mushabac
U.S. Pat. No. 5,740,802 to Nafis
U.S. Pat. No. 5,792,147 to Evans
U.S. Pat. No. 5,836,954 to Heilbrun
U.S. Pat. No. 5,954,650 to Saito
U.S. Pat. No. 6,006,126 to Cosman
U.S. Pat. No. 6,381,485 to Hunter
U.S. Pat. No. 6,450,978 to Brosseau
U.S. Pat. No. 6,919,867 to Sauer
U.S. Pat. No. 6,978,167 to Dekel
U.S. Pat. No. 7,376,903 to Morita
US 2004/0002642 to Dekel
US 2004/0210125 to Chen
US 2006/0240378 to Weinstein
US 2007/0208252 to Makower
US 2008/0055308 to Dekel
US 2008/0074422 to Dekel
US 2008/0278490 to Dekel
US 2009/0042167 to Van Der Zel
US 2009/0092948 to Gantes
US 2009/0097722 to Dekel
WO 91/07726 to Greenberg
WO 06/076789 to Dekel

SUMMARY OF EMBODIMENTS

For some applications, the apparatus and methods described herein are used for facilitating the co-use of two or more imaging modalities for navigation during a dental procedure, and/or for planning a dental procedure. Typically, the apparatus and methods provided herein facilitate the co-use of CT images and optical images (which, for example, are acquired using a digital camera). Alternatively or additionally, the apparatus and methods provided herein facilitate the co-use of orthopantogram (OPG) images and optical images (which, for example, are acquired using a digital camera). In general, techniques described hereinbelow with respect to CT imaging may be carried out using OPG (in particular if bone thickness is sufficient, and/or in combination with OPG-suitable measurement techniques, such as periapical x-ray imaging performed when a marked depth-measuring tool is inserted into an osteotomy).

For some applications, the apparatus and techniques provided herein are used to facilitate drilling and location of dental implants. For example, the techniques described herein may be used, at the planning stage of a procedure, to determine suitable location, orientation, and depth for a dental implant. Typically, at the planning stage of a procedure, a CT image of the subject's jaw is generated. In addition, optical images are generated in order to generate optical data of the mouth. The CT data are combined with the optical data to determine how to drill and in what orientation, and to what depth. Typically, optical data provide information regarding anatomy that is exposed, such as teeth. CT data (that show underlying bone structure) are combined with optical data (that show visible anatomy), in order to facilitate planning of the procedure.

Subsequently, during the implantation procedure, the techniques described herein may be used to navigate the implant to the determined location, orientation, and depth. Further subsequently, the techniques described herein may be used to ascertain the implantation location, orientation, and depth of the implant. Alternatively or additionally, the apparatus and techniques provided herein are used in orthodontic procedures, for example, to facilitate placement of orthodontic braces.

For some applications, the techniques described herein are used to navigate a syringe to the mandibular nerve, in order to administer anesthetic to the mandibular nerve. For example, a CT scan of an area of the mandibular foramen (for example, at the entrance of the mandibular nerve into the mandibular bone) may be performed. The syringe may be identified in the CT scan by touching one or more points (e.g., teeth) that are visible on the CT scan with the syringe, and/or by identifying radiopaque markers on the syringe. The syringe may also include visual markers that are used to identify the syringe in optical images of the syringe. Thus, the syringe may be used as a fiducial for registering the optical images to the CT images.

For some applications, the apparatus and techniques provided herein are used to facilitate preparation for placing a bridge. For example, a drill that includes optical and/or radiopaque markers may be used to ascertain that all prepared teeth are parallel to each other. A camera that is placed inside or outside the subject's mouth may be used to image the drill.

There is therefore provided, in accordance with some applications of the present invention, apparatus, including:
  at least one tool configured to be placed inside a mouth of a subject;
  a first optically-visible marker that is coupled to the tool;
  a second optically-visible marker configured to be coupled to a structure inside the subject's mouth;
  a plurality of optical cameras that are coupled to the tool, and that are configured to:
    be placed inside the subject's mouth by the tool being placed inside the subject's mouth, and
    acquire respective images of the inside of the subject's mouth, in which the second optically-visible marker is identifiable; and
  a plurality of optical cameras that are disposed outside the subject's mouth and that are configured to acquire respective images of the tool, while the tool is inside the subject's mouth, in which images the first optically-visible marker is identifiable.

There is further provided, in accordance with some applications of the present invention, a method including:
  placing a first marker on a structure inside a mouth of a subject, the marker being optically-visible and radiopaque;
  while the marker is disposed on the structure, acquiring at least two optical images of the structure, using respective cameras; and
  determining a location of the marker in the optical images.

For some applications, the method further includes acquiring a CT image of the structure, and registering the CT image to the optical images, by identifying the location of the marker in the CT image.

For some applications, acquiring the optical images includes acquiring the optical images using cameras that are coupled to a tool, while the tool is disposed inside the subject's mouth, and determining the location of the marker in the images includes identifying a position of the tool with respect to the structure by determining the location of the marker in the optical images.

For some applications,
  the method further includes placing a tool inside the subject's mouth, the tool having coupled thereto a second optically-visible marker,
  and:
    acquiring at least two optical images of the structure includes acquiring at least two optical images of the tool inside the subject's mouth; and
    determining the location of the marker in the images includes determining a position of the tool with respect to the structure by determining locations of the first and second markers.

For some applications, placing the marker on the structure includes placing onto the subject's teeth a moldable sheet configured to take an impression of the subject's teeth, the marker being coupled to the sheet.

For some applications,
  the method further includes generating a plan of a procedure to be performed in the subject's mouth using a three-dimensional image of the subject's mouth,
  and determining the location of the marker in the images includes registering the plan to the optical images of the structure by determining the location of the marker in the images.

For some applications, the method further includes updating the plan of the procedure, in response to the registration.

For some applications,
  the structure includes a tooth, and
  the method further includes:
  generating a three-dimensional image of a least a portion of the subject's mouth; and
  determining a location of the tooth with reference to teeth that surround the tooth, by identifying the marker in the three-dimensional image and in the optical images.

For some applications, placing the marker on the tooth includes placing the marker such that a first portion of the marker is above a gingiva of the subject, and a second portion of the marker is below the gingiva.

There is further provided, in accordance with some applications of the present invention, apparatus, including:
  a moldable sheet configured to take an impression of teeth of a subject by being placed on the subject's teeth; and
  a marker that is optically-visible and radiopaque, coupled to the sheet.

There is additionally provided, in accordance with some applications of the present invention, a method, including:
  placing onto teeth of a subject a moldable sheet configured to take an impression of the subject's teeth, there being an optically-visible, radiopaque marker coupled to the sheet;
  generating CT images of the subject's teeth, while the sheet is disposed on the teeth;
  determining a position of the sheet in the CT image, by identifying the marker in the CT image.

There is further provided, in accordance with some applications of the present invention, apparatus, including:
  a dental implant;
  a prosthetic element configured to be coupled at least temporarily to the dental implant; and
  a radiopaque marker coupled to the prosthetic element.

For some applications, the marker is optically-visible.

For some applications, the prosthetic element includes a gingival former.

For some applications, the prosthetic element includes an abutment.

For some applications, the apparatus further includes:

an imaging device configured to generate a three-dimensional image of the prosthetic element; and a processor configured to determine a location of the implant by identifying the marker in the three-dimensional image.

There is further provided, in accordance with some applications of the present invention, apparatus, including:

a support element configured to be coupled to a fixed structure inside a mouth of a subject; and a marker that is reversibly couplable to the support element, such that:

the marker is disposed at a predefined orientation with respect to the fixed structure, and the marker facilitates identification of an orientation of the fixed structure in images of the subject's mouth.

There is additionally provided, in accordance with some applications of the present invention, a method, including:

temporarily coupling a mechanical element to a fixed structure inside a mouth of a subject;

using the mechanical element to orient a marker at a predefined orientation with respect to the fixed structure, by reversibly coupling the marker to the mechanical element; and identifying an orientation of the fixed structure based on an orientation of the marker.

For some applications, temporarily coupling the mechanical element to the fixed structure includes removing the mechanical element more than 15 minutes after coupling the mechanical element to the fixed structure.

For some applications, temporarily coupling the mechanical element to the fixed structure includes removing the mechanical element less than one month after coupling the mechanical element to the fixed structure.

For some applications, temporarily coupling the mechanical to the fixed structure element includes removing the mechanical element less than one month after coupling the mechanical element to the fixed structure.

The present invention will be more fully understood from the following detailed description of embodiments thereof, taken together with the drawings, in which:

DETAILED DESCRIPTION OF EMBODIMENTS

Figure 1:
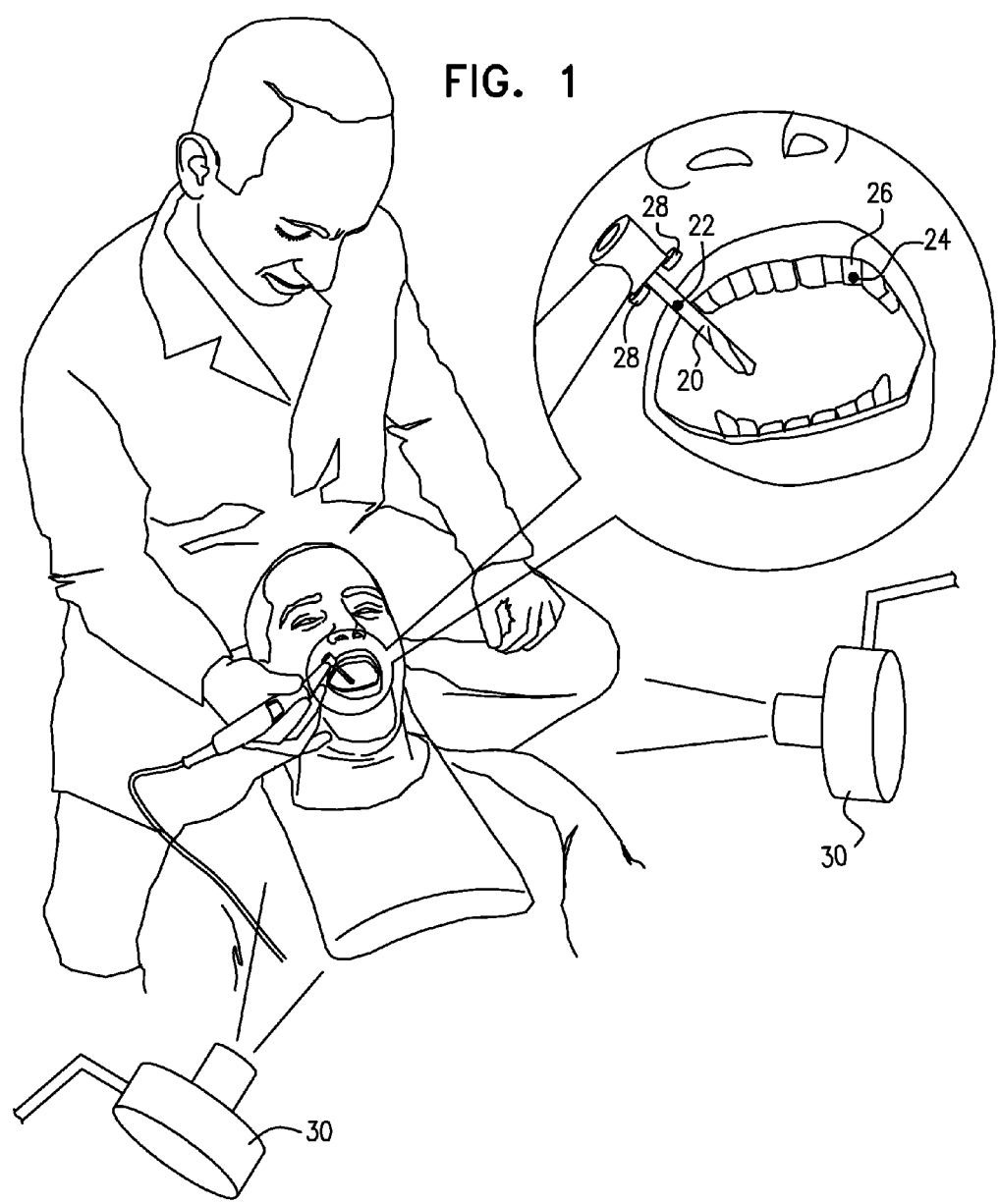
FIG. 1 is a schematic illustration of optically-visible, radiopaque markers coupled to a dental tool and to a structure inside a subject's mouth, in accordance with some applications of the present invention.

Reference is now made to FIG. 1, which is a schematic illustration of a dental tool 20 that has a first optically-visible marker 22 (i.e., a marker that is identifiable in an optical image) attached thereto, in accordance with some applications of the present invention. In addition, a second optically-visible marker 24 is attached to a structure 26 (e.g., a tooth as shown) inside a subject's mouth. Two or more tool-cameras 28 are coupled to the tool at a fixed position with respect to the tool. The position of the tool with respect to tooth 26 is determined by identifying (for example, using a processor that is in communication with the tool-cameras) optical marker 24 in images that are acquired by the tool-cameras. Two or more external cameras 30, which are located outside the subject's body, acquire images of the tool. The location of the tool with respect to a fiducial is identified (for example, using a processor that is in communication with the external cameras) in the images acquired by the external cameras, by identifying the first optical marker in the images. By determining the position of tool 20 with respect to tooth 26, in addition to determining the position of the tool with respect to the fiducial, the position of the tooth with respect to the fiducial is determined.

By using the determined positions of tool 20 and tooth 26 with respect to the fiducial, the optical images acquired by tool-cameras 28, and/or external cameras 30 may be registered to images acquired using a different imaging modality, in which the fiducial is identifiable. For example, the fiducial may be a radiopaque fiducial that is identifiable in x-ray images. Thus, CT images of the subject's mouth may be registered to the optical images, by identifying the fiducial in the CT images.

For some applications, first marker 22 and/or second marker 24 is identifiable in both optical images and in the images acquired using the different modality. Typically, first marker 22 and/or second marker 24 are radiopaque, and are therefore identifiable in CT images, in addition to being identifiable in optical images, as described hereinabove. Thus, for some applications, first marker 22 and/or second marker 24 may act as a fiducial for registering optical images of the subject's mouth to X-ray images (e.g., CT images) of the subject's mouth.

For some applications, only one of markers 24 and 26 is used. The position of the marker is identified in optical images acquired by external cameras 30 and/or by tool-cameras 28, and in CT images acquired by a CT scanner. Thus, the CT images are registered to the optical images.

For some applications, first marker 22 and/or second marker 24 have distinctive shapes, in order to facilitate identification of the markers in optical and/or x-ray images of the markers. For example, the markers may be pieces of metal shaped as crosses, stars, stripes, and/or other shapes, as would be obvious to one skilled in the art, having read the specification of the present patent application.

Figure 4:
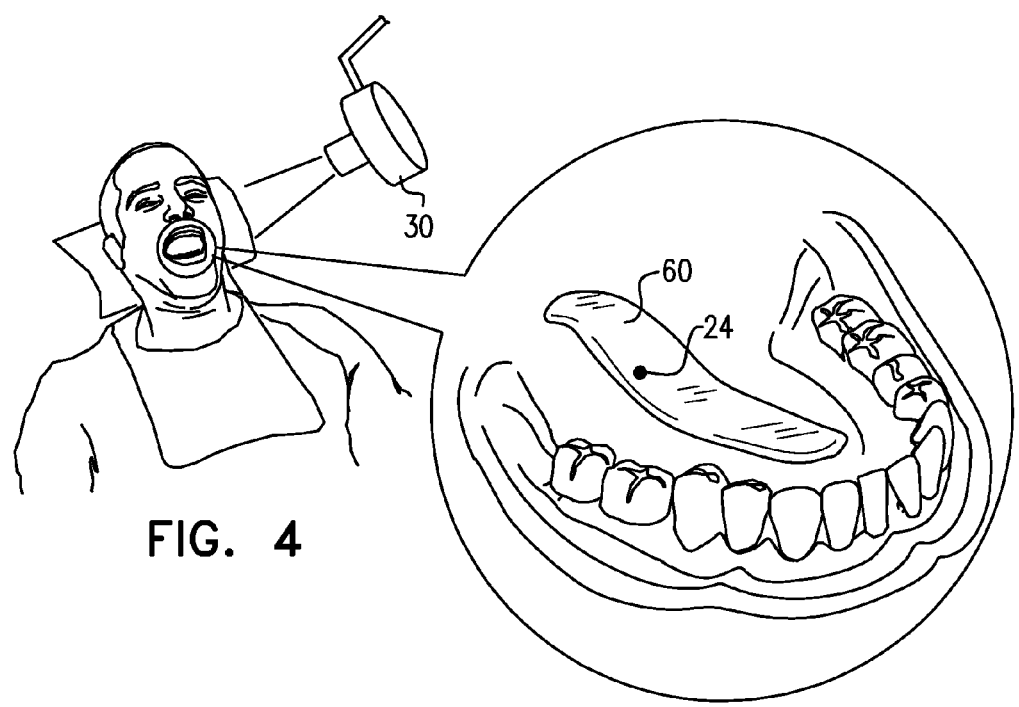
FIG. 4 is a schematic illustration of a moldable sheet configured to take an impression of a subject's teeth, an optically-visible, radiopaque marker being coupled to the sheet, in accordance with some applications of the present invention.

For some applications, one or more laser beams (e.g., a plurality of parallel laser beams) that are optically-visible are used as fiducials and/or as marker 24 or 26. The laser beams are used for registering optical images to CT images, in accordance with the techniques described herein. For some applications, second marker 24 is placed on a structure that is temporarily placed inside the subject's mouth, such as a bridge. For example, marker 24 may be prefabricated on or within a bridge. Or, second marker 24 may be prefabricated on a sheet that is placed on the subject's teeth in order to take an impression of the teeth, as shown in FIG. 4. While the sheet is on the teeth, the optical images of the teeth are registered with CT images of the teeth, via the marker.

Alternatively, as shown in FIG. 1, second marker 24 is placed on a tooth. For example, the marker may be placed on a tooth that has been prepared for crown and/or bridge work. Optical images and CT images of the tooth and the surrounding teeth are registered to each other using the techniques described herein, using the marker as a fiducial for the registration. For some applications, marker 24 is placed such that a first portion of the marker is above the gingiva, and a second portion of the tag is below the gingiva.

For some applications, in a planning stage of a dental procedure, a drilling-plan is generated on previously-acquired CT images of the subject's teeth. Subsequently, during the procedure, a drill (corresponding to tool 20 in FIG. 1) is inserted into the subject's mouth. The position of marker 22 with respect to a fiducial is used to register the current position of the tool with respect to the CT images on which the drilling-plan was generated. Alternatively or additionally, the position of marker 24 with respect to a fiducial is used to register the current position of the dental structure 26 with respect to the CT images on which the drilling-plan was generated. For some applications, the drilling-plan is updated during the procedure, in response to the currently-determined location of the drill and/or structure 26 with respect to the previously-generated drilling-plan.

For some applications, during an implantation procedure, tool 20 is placed on a dental implant in order to facilitate location of the implant in optical and/or CT images of the patient's mouth. Typically, if, based upon the identification of the tool, it is determined that the implant is not placed at a desired position, orientation, and/or depth, the implant is removed and/or is re-implanted at the desired position, orientation, and/or depth. For some applications, in response to identifying the location of the implant, suitable locations for further implants are determined.

Figure 2:
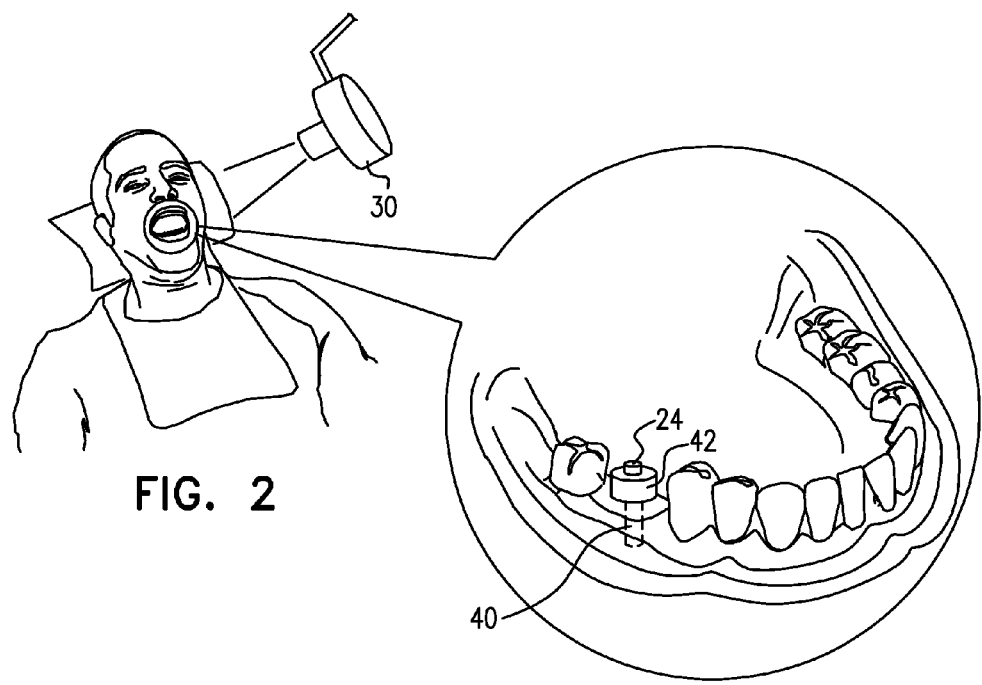
FIG. 2 is a schematic illustration of an optically-visible, radiopaque marker coupled to a prosthetic element inside a subject's mouth, in accordance with some applications of the present invention.

Reference is now made to FIG. 2, which is a schematic illustration of marker 24 placed on a prosthetic element 42 that is coupled to a dental implant 40, in accordance with some applications of the present invention. In accordance with respective applications, prosthetic element 42 may include an abutment, a gingiva former, and/or a different prosthetic element. For some applications, marker 24 is used to determine the location, orientation, and/or depth of implant 40 with respect to the surrounding teeth, for example, in order to facilitate the planning of the placement of a crown on the implant.

Figure 3:
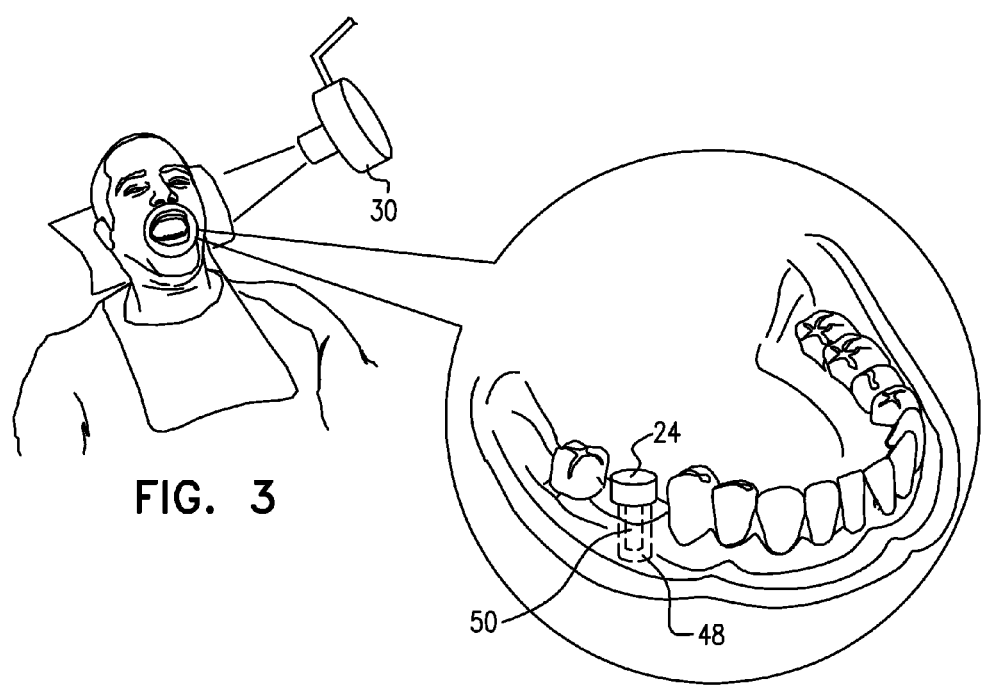
FIG. 3 is a schematic illustration of an optically-visible, radiopaque marker coupled to a plug that has been inserted into a hole drilled in a subject's mouth, in accordance with some applications of the present invention.

Reference is now made to FIG. 3, which is a schematic illustration of marker 24 placed on a plug 50 that is temporarily placed inside a drilled hole 48. For some applications, marker 24 is used to determine the location, orientation, and/or depth of hole 48 with respect to the surrounding teeth, for example, in order to ascertain that the hole was drilled in accordance with a drilling-plan.

For some applications, a marker (e.g., a marker that is optically-visible and/or radiopaque) is coupled to tooth 26 of the subject, in order to facilitate identification of the orientation of the subject's mouth in two or more images that are acquired at respective times. For example, in the course of a dental or an orthodontic treatment, a subject's teeth may be imaged at weekly or monthly intervals, in order to determine the progress of the treatment. By determining the orientation of the subject's mouth by means of the marker, the images can be compared to each other.

For some applications, in between the acquisitions of the images, it is not desirable for the marker to be coupled to the subject's tooth. For example, the marker may be a relatively large marker (e.g., in order to facilitate identification of the marker in the images) that causes the subject discomfort if it is inside the subject's mouth for an extended period of time. Therefore, for some applications, a mechanical element such as a small support element is coupled to a fixed structure (such as tooth 26) inside the subject's mouth. The marker is couplable to the support element, such that when the marker is coupled to the support element, the marker is oriented at a fixed orientation with respect to the fixed structure inside the subject's mouth. The marker is coupled to the support element before an image is acquired, and is decoupled from the support element and removed from the subject's mouth in between images.

For some applications, the support element is similar to an orthodontic bracket. Typically, when the course of treatment is terminated, the support element is removed from the fixed structure inside the subject's mouth. For some applications, the support element is coupled to the fixed structure inside the subject's mouth during the course of the treatment for a period of more than 15 minutes, e.g., for more than one day, more than one week, or even more than two weeks. (Typically, however, the support element is coupled to the fixed structure for a period (such as less than two weeks) that is shorter than would be generally used for orthodontic work.) During this period, the marker is typically coupled to the support element for periods of less than two hours, less than one hour, or less than 15 minutes, while the subject's mouth is imaged. For some applications, the support element also acts as a marker in the images, but, for example, the large marker may be more identifiable than the support element in the images.

FIG. 4 is a schematic illustration of a moldable sheet 60 configured to take an impression of a subject's teeth, optically-visible, radiopaque marker 24 being coupled to the sheet, in accordance with some applications of the present invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   at least one tool configured to be placed inside a mouth of a subject;
   a first optically-visible marker that is coupled to the tool;
   a second optically-visible marker configured to be coupled to a structure inside the subject's mouth;
   a plurality of optical cameras that are coupled to the tool, and that are configured to:
     be placed inside the subject's mouth by the tool being placed inside the subject's mouth, and
     acquire respective images of the inside of the subject's mouth, in which the second optically-visible marker is identifiable; and
   a plurality of optical cameras that are configured to be positioned outside the subject's mouth and that are configured to acquire respective images of the tool, while the tool is inside the subject's mouth, in which images the first optically-visible marker is identifiable.

2. A method comprising:
   placing a first marker on a structure inside a mouth of a subject, the marker being optically-visible and radiopaque;
   while the marker is disposed on the structure, acquiring at least two optical images of the structure, using respective cameras;
   determining a location of the marker in the optical images;
   the method further comprising placing a tool inside the subject's mouth, the tool having coupled thereto a second optically-visible marker, wherein:
acquiring at least two optical images of the structure comprises acquiring at least two optical images of the tool inside the subject's mouth, and
determining the location of the marker in the images comprises determining a position of the tool with respect to the structure by determining locations of the first and second markers.

3. The method according to claim 2, further comprising acquiring a CT image of the structure, and registering the CT image to the optical images, by identifying the location of the marker in the CT image.

4. The method according to claim 2, wherein placing the marker on the structure comprises placing onto the subject's teeth a moldable sheet configured to take an impression of the subject's teeth, the marker being coupled to the sheet.

5. The method according to claim 2,
further comprising generating a plan of a procedure to be performed in the subject's mouth using a three-dimensional image of the subject's mouth,
wherein determining the location of the marker in the images comprises registering the plan to the optical images of the structure by determining the location of the marker in the images.

6. The method according to claim 5, further comprising updating the plan of the procedure, in response to the registration.

7. The method according to claim 2,
wherein the structure includes a tooth,
further comprising:
generating a three-dimensional image of at least a portion of the subject's mouth; and
determining a location of the tooth with reference to teeth that surround the tooth, by identifying the marker in the three-dimensional image and in the optical images.

8. The method according to claim 7, wherein placing the marker on the tooth comprises placing the marker such that a first portion of the marker is above a gingiva of the subject, and a second portion of the marker is below the gingiva.

* * * * *